(12) United States Patent
Poppen et al.

(10) Patent No.: US 6,248,159 B1
(45) Date of Patent: *Jun. 19, 2001

(54) WOOD PRESERVATIVE

(75) Inventors: Heinrich Poppen; Michael Pallaske, both of Löningen (DE)

(73) Assignee: Rohm and Haas Company, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/457,539

(22) Filed: Dec. 9, 1999

Related U.S. Application Data

(62) Division of application No. 09/043,837, filed on Jun. 9, 1998, now Pat. No. 6,123,756.

(30) Foreign Application Priority Data

Sep. 29, 1995 (DE) ............................... 195 36 328
Jul. 20, 1996 (DE) ............................... 196 29 345

(51) Int. Cl.⁷ ............................ C09D 5/14; C09K 15/22; A01N 25/34; A01N 43/64
(52) U.S. Cl. .................. 106/15.05; 106/18.32; 106/12; 252/403; 252/380; 424/413; 424/84; 424/405; 424/78.09; 514/359; 514/383; 427/440
(58) Field of Search ................. 424/78.09, 413, 424/84, 405; 252/380, 403; 106/15.05, 12, 18.32; 427/440; 514/359, 383

(56) References Cited

U.S. PATENT DOCUMENTS

| | | | |
|---|---|---|---|
| 3,910,894 | 10/1975 | Wah Wat | 549/554 |
| 4,656,189 | 4/1987 | Bowers | 514/456 |
| 5,196,407 | 3/1993 | Goletz et al. | 514/63 |
| 5,248,450 | 9/1993 | Metzner et al. | 252/380 |
| 5,308,859 | 5/1994 | Metzner et al. | 514/383 |
| 5,434,181 | 7/1995 | Kodaka et al. | 514/471 |
| 5,714,507 | 2/1998 | Valcke et al. | 514/383 |
| 5,804,591 | 9/1998 | Valcke et al. | 514/383 |

FOREIGN PATENT DOCUMENTS

| | | |
|---|---|---|
| 3420230 | 1/1986 | (DE) . |
| 1233205 | 9/1989 | (JP) . |
| 0428804 | * 10/1992 | (JP) . |

OTHER PUBLICATIONS

"Use of the Insecticide Fenoxycarb as a Wood Preservative." Chemical Abstracts, vol. 117, No. 14 (Oct. 5, 1992).

Research Disclosure, No 338 (Jun. 1992).

Derwent Abstract of JP 01 233 205 of Sep. 19, 1989.

* cited by examiner

Primary Examiner—Arlen Soderquist
Assistant Examiner—Monique T. Cole
(74) Attorney, Agent, or Firm—Ladas & Parry

(57) ABSTRACT

A wood protecting agent, particularly for the protection of wood against dry-wood-destroying insects is provided. The wood protecting agent comprises a wood preservative carrier and the combination of at least one insect juvenile hormone or its analogue or mimetic with at least one an ecdysone agonist or its analogue or mimetic in a concentration of 0.5 to 0.00005 % by weight, related to the entire formulation, and optionally, one or more triazole compounds to achieve a synergistic increase in effectiveness of said formulation.

10 Claims, No Drawings

WOOD PRESERVATIVE

This application is divisional of copending application(s) application Ser. No. 09/043,837 filed on Jun. 9, 1998, U.S. Pat. No. 6,123,756 Sep. 26, 2000 claims the benefit thereof and incorporates the same by reference.

The invention relates to a wood preservative which is particularly suitable for the protection of wood against wood-attacking insects. The preservative contains the usual carriers and aids and is suitable both for the preventive protection of wood as well as for combating an existing outbreak.

For the protection of wood against destruction and quality impairment due to attack by injurious organisms, particularly insects and fungi, chemicals with biocidal action have been used extensively to combat the respective injurious organisms. Use also has been made of insecticides such as neurotoxins which have a non-specific action mechanism, and the potential to effect the environment adversely. For this reason, most of the preparations used so far have demonstrated more or less pronounced drawbacks as regards their environmental compatibility when inexpertly used.

There is therefore a great need for environmentally compatible wood protective agents which, in the event of inexpert use, reduce to the technically achievable minimum the danger of such agents to the health of operators and end consumers. The manner in which biological or biogenic wood preservatives has been used has not so far been seen to lead to an achievement of the aim. All the substances offered so far as "biological wood preservatives", which contain, for example, balsam terpentine oil and wood vinegar have not been able to meet the demands made on wood preservatives. Particularly, against the main wood destroyers, the house longhorn (*hylotrupes bajulus*), woodworm (*anobium punctatum*) and bark beetle (*lyctus brunneus*), it is still necessary to use highly active chemicals.

The use of insect hormones against an insect attack has long been known from integrated plant protection studies. In particular, use has been made of analogues and mimetics of moult and cocoon hormones, that is, insect juvenile hormone analogues and ecdysone agonists. These agents, because of their hormonal character, are used in the lowest application concentrations, and are highly selectively insect active, the selectivity being so specific that only individual orders of insects such as beetles are covered, and useful insects in other orders such as hymenopters are very largely spared.

These agents have not yet been used in wood preservation, as this group of active substances had not yet been available and organo-chlorine insecticides and synthetic pyrethroids were popularly used for this purpose. In addition, as there were drawbacks still attached to the use of first generation insect hormonal analogues (higher steam pressure, hydrolysis instability), these agents did not come into consideration as wood preservatives.

The object of the invention is to provide a wood preservative which is at least equivalent to the preservatives being used currently and which meets present-day environmental compatibility and toxicology standards. The agent should be long-lasting and afford reliable protection, particularly against attack by wood-destroying insects. Furthermore, the wood impregnated with the agent should, after the useful life of the construction expires, be re-usable without problems or consequences for the environment.

The present invention provides a wood preservative which contains one or more insect hormones and/or their analogues or mimetics, which control egg development, moulting or cocooning of insects, in a concentration of 0.00005 to 0.5 weight %, based on the total weight of the composition. The composition also may contain triazole compounds, particularly triazole fungicides, the combination bringing about a synergetic effect.

According to the invention, insect hormones which may be used include juvenile hormones and ecdysone as well as their analogues and mimetics.

These hormones have an effect on the hormonal control systems of insects, controlling embryonal development in the fertilized egg, moulting in the larval stage, and, at the end of the larval stage, cocooning and development to the mature organism. As long as the juvenile hormone is present, the insect remains in the larval stage, with individual moultings being induced by additional ecdysis. After the drop of the juvenile hormone level at the end of the larval phase, ecdysis brings about cocooning.

The introduction of the insect hormone into the hormonal control system therefore may be used for combating harmful insects. It is known that juvenile hormones can have an ovicidal action. Furthermore, their action on the fully developed larva leads to an artificial prolongation of the larval stage, to excessive moulting and finally to the dying of the larvae. Use of ecdysone on insect larvae results in a number of spontaneous moultings and mostly to the dying off of the larvae. The use of an excessive amount of ecdysone and/or ecdysone agonist induces a forced premature cocooning and metamorphosis to deformed adult insects which are unable to reproduce. The targeted use of insect hormones disturbs or prevents the multiplication of insects either by ovicidal action or by interference with the formation of the mature insect. In addition, these insect hormones interfere also with the control systems of the mature insect and can set off malfunctions such as chemosterilization.

Along with the actual juvenile hormones and ecdysones a number of analogues and mimetics were developed which exert a comparable action upon the hormonal control systems of insects. Such analogues and mimetics include structurally related compounds, that is, derivatives of ecdysones and juvenile hormones, and also chemical compounds which in spite of being structurally different in nature have a comparable effect. A great number of analogues, particularly of the juvenile hormones, have been developed. According to the invention, the insect juvenile hormones and ecdysteroids, their mimetics and analogues, can be used alone or in combination. According to the invention, each of the hormones or its analogues or mimetics is present in an amount in the range of 0.00005 to 0.5 weight % based on the weight of the entire formulation. Preferably, the concentration of each hormone or active agent in the formulation is 0.001 to 0.005% b.w.

Juvenile hormone analogues suitable for use in the invention are:

Pyriproxyphene: 4-phenoxyphenyl-(RS)-2-2(2-pyridyloxy) propyl ether,

Fenoxycarb: Ethyl {2-(4-fenoxyfenoxy)ethyl} carbamate,

Kinoprene: 2-propynyl-(E)-3,7,11-trimethyl-2,4-dodecadienoate,

Methoprene: Isopropyl-(2E, 4E)-11-methoxy-3,7,11-trimethyl-2,4-dodecadienoate,

Hydroprene: ethyl-(E,E)-(R,S)-3,7,11-trimethyldodeca-2,4-dienoate.

Of the above, pyriproxyphene and fenoxycarb are preferred juvenile hormone analogues.

Ecdysone agonists suitable for use are:

Tebufenozide: N-tert-butyl-N'-(4-ethylbenzoyl) propylether,

RH-0345®: halofenozide; benzoic acid, N-tert-butyl-N-(4-chlorobenzoyl)-hydrozide; a coleopter specific variant of tebufenozide, RH-5849®: a tebufenozide analogue; N-tert-butyl-N-(4-ethylbenzoyl)-3,5-dimethyl benzohydrozide; a beetle specific alternative to tebufenozide Azadirachtin or Azadiractanin.

Of the above, tebufenozide and RH-0345® are preferred ecdysone agonists. The use of a combination of two juvenile hormone analogues pyriproxyphene and fenoxycarb is particularly preferred. The two agents complement each other in their effect in optimum fashion in that fenoxycarb displays effectiveness against the wood-harming insects especially at the embryonic stage and during metamorphosis, while pyriproxyphene is effective also during the larval stage. The combination of these two agents makes it possible to attack insects during the entire period of insect development. The ovicidal action of fenoxycarb is particularly effective on the eggs of the house longhorn.

Also preferred is the combination of at least one juvenile hormone analogue with an ecdysone agonist as this combination imitates the natural prerequisites for the moulting of larva and mature insects independent of the developmental condition of the larva. The repeated, untimely moultings lead to a premature dying off of the larva, that is, a drastic shortening of the extremely lengthy larval stages (from 2 up to 12 years) of wood insects, thereby minimizing damage to wood caused by the insects. At the same time, the presence of the juvenile hormone prevents the development of the embryo in the egg, so that the development of the insect population is effectively disturbed and a new incidence of insect attack can be reliably avoided.

The wood preservative of the invention also may include a fungicide, particularly a triazole fungicide which, in addition to its own fungicidal action, displays a synergetic activity together with the hormone components in that the action of the insect hormone is enhanced, or the response threshold to the hormone is lowered. It is believed that triazoles in combination with the hormones bring about the synergetic effect by increasing the permeability of the insect cell membrane to the insect hormone. This makes it possible to use the insect hormone in smaller concentrations than if the hormone were used without the triazole compound.

Preferred fungicides for use in the invention are known triazole fungicides such as:

Propiconazole: 1-(2,4-dichlorophenyl)-4-propyl-1,3-dioxolane-2-yl)-methyl)-1H-1,2,4-triazole, Tebuconazole: alpha-{2-(4-chlorophenyl)ethyl} -alpha-(1,1-dimethylethyl)-1H-1,2,4-triazole-1-ethanol, Azaconazole: 1-{2,4-dichlorophenyl)-1,3 -dioxolane-2-yl-methyl}-1H-1,2,4-triazole, Phenbuconazole: (RS)-4-4(4-chlorophenyl)-2-phenyl-2-(1H-1,2,4-triazole-1-yl-methyl)butyronitrile, Myclobutanil: alpha-butyl-alpha-4(4-chlorophenyl)-1-1,2,4-triazole-1-propene nitrile, Triadimenol: 1 -(4-chlorophenyl)-3,3-dimethyl-1-(1H-1,2,4-triazole-1 -yl-methyl)-butane-2-ole.

These triazole fungicides are typically added in an amount of 0.15 to 1.5% b.w., preferably 0.4 to 0.8% b.w, related to the entire ready to use formulation.

Also suitable for use in the invention are non-triazole fungicides, the same concentrations being used in the wood preservative as given for the triazole fungicides, such as:

Nuarimol: alpha-(2-chlorophenyl)-alpha-(4-fluorophenyl)-5-pyrimidine methanol,

Phenarimol: alpha-(2-chlorophenyl)-alpha-(4-chlorophenyl)-5-pyrimidine methanol, IPBC: 3-iodopropargyl-N-butyl carbamate, Tolylfluanide: N'-dichlorofluoromethylthio-N,N-dimethyl-N'-tolyl sulphamide, Dichlofluanide: N'-dichlorfluoromethylthio-N,N-dimethyl-N'-phenyl sulphamide, TIAA: 2,3-3-triiodallyl alcohol.

Other suitable non-triazole fungicides are:

XYLIGEN A1®: tris-(N-cyclohexyldiazeniumdioxy)-aluminum,

Cu-HDO: N-Nitroso-N-cyclohexyl-hydroxylamine-copper, quaternary ammonium compounds, Betaine: didecylpolyoxyethyl ammonium borate, polychlorinated hydrocarbons such as PCP, Boron compounds such as boric acid or borax, wherein the concentration, in the ready-to-use formulation, is about 0.1 to 10% b.w., preferably 0.5 to 5% b.w.

In addition, it is possible to use both boron compounds, for example boric acid or borax, and quaternary ammonium compounds, such as trimethyldecylammonium chloride, in a total amount of 1 to 50% b.w., preferably 5 to 25% b.w., based on the weight of the entire formulation. Quaternary ammonium compounds possess, in addition to their fungicidal and bactericidal action, the property of stabilizing the compositions of the invention by holding the active substances in aqueous suspension and protecting them against biological decomposition in timber built in contact with earth. Quaternary ammonium components promote the impregnation effect and ensure a particularly deep penetration into the substance of the wood where they contribute to the immobilization of the active substances.

The compositions of the invention contain, in addition to the active components, at least one carrier substance in solid or liquid form, that is, a thinner or a solvent. Binding agents and other additives may also be added.

The compositions of the invention also may include, for example, fixing agents, softeners, emulsifiers, cross-linking agents, solution mediators as well as agents promoting processing. Pigments, dyes, anti-corrosion agents, odor correctors, pH-regulators, and UV-stabilizers also may be added.

The wood preservatives of the invention may be present as concentrates or as ready-to-use mixtures. Suitable formulations for coatings, impregnation agents, spraying agents as well as agents for pressure impregnation will be known to those of skill in the art. The usual methods, such as painting, spraying, atomizing, dipping; impregnation processes such as soaking, dipping, pressure, vacuum or double vacuum processes may be used to introduce the formulations of the invention to the wood to be treated.

Solvents useful in the compositions of the invention include both polar and non-polar organic solvents, water or mixtures of the foregoing, depending on the application process used and the active agent or combination of agents used. The use of aqueous or organic-aqueous solutions, emulsions and/or suspensions for the purposes of the invention is preferred. To increase or improve the solubility of the agents in the liquid carrier emulsifiers or solubilizers may be employed.

Preferred polar organic solvents are those which contain hydroxy, ether, keto or ester groups. Particularly suitable polar organic solvents are alcohols, glycols, glycoetherm diacetone alcohol, water-insoluble polyols and their esters.

Suitable non-polar solvents are aliphatic or aromatic hydrocarbons.

In particular, low volatility or non-volatile water-insoluble oily or oily-type solvents with an evaporation rate above 35 and a flash point above 30° C., preferably above 45° C., can be used. Such solvents include minerals oils or their aromatic fractions or mixtures of solvents containing mineral oils, preferably solvent naphtha, spindle oil, petroleum, terpentine oil, terpene hydrocarbons, aromate-free petroleum fractions or alkyl benzenes.

Organic binding agents suitable for use within the framework of the present invention in the above-mentioned organic solvents are soluble or dispersible or emulsifiable synthetic resins or binding siccative oils, particularly binders which consist of acrylate resin, a vinyl resin, for example, polyvinyl acetate, a polyester resin, polycondensation or polyaddition resin, polyurethane resin, alkyd resin, silicon resin, drying vegetable or synthetic oils or physically drying binding agents based on a natural or synthetic resin.

Preferred binding agents include synthetic resins in the form of an emulsion, dispersion or solution, preferably alkyd resins or modified alkyd resins or phenol resins, and also hydrocarbon resins, preferably indene-cumarone resins. Other useful binders are bitumen or bituminous substances, used in amounts of up to 15% b.w.

As an alternative or in addition to binders, fixing agents and/or softeners may be used.

Emulsifiers suitable for use in the inventive compositions are, for example, anionic or cationic emulsifiers, and also mixtures of emulsifiers, such as alkyl, aryl and alkyl aryl sulphonates, phosphoric acid partial esters, and quaternary ammonium compounds.

However, it is preferred to use nonionic emulsifiers, alone or mixed, such as, alkyl polyglycol ethers or esters or alkylaryl polyglycol ethers or esters, alkyl phenolpolyglycol ether, polyoxyethylene derivatives, carboxylic acid polyethylene glycol esters, alkylol amide, a side group-containing ethoxylated phenols, particularly ethoxylated nonyl phenol, or ethoxylated fatty acids, and also fatty acids esters of polyhydroxy compounds, particularly mono- and di-fatty acid esters of glycerine, polyglycerine or glycerine polyethylene or polypropylene glycol ethers.

Emulsifiers may be combined with cross-linking agents, for example, those based on phosphoramine compounds.

For the preparation of emulsion concentrates or hydrated wood preservatives it is preferred to use polar organic solvents, preferably those with hydroxyl, ether or keto groups, for example, ethylene and propylene glycol, the oligomers and the monoalkyl ethers of same, particularly of ethylene glycol, diethylene glycol, ethyl glycol, butyl glycol, and ethyl diglycol. Diacetone alcohol is particularly suitable.

Useful solubilizers include those that are anion active or cation active, or preferably, nonionic surfactants, which convert the active substances in water into a stable emulsion.

Examples of anionic surfactants include alkyl, aryl and alkylaryl sulphonates. Cationic surfactants include quaternary ammonium compounds. Examples of nonionic surfactants are alkyl polyglycol ethers or esters and alkyl aryl polyglycol ethers or esters, polyoxyethylene derivatives, ethoxylated nonyl phenol, fatty acid esters of polyhydroxy compounds, particularly mono- and di-fatty acids esters of glycerine, polyglycerine or glycerine polyethylene or polypropylene glycol ethers.

The agents of the invention may also contain per se known dyes, pigments, water-repellent agents, odor correctors and inhibitors, anti-corrosion agents and the like. The compositions of the invention also may include an amino alcohol for pH regulation and/or as a co-emulsifier, particularly mono or diethylamine.

For specific recipes it may be appropriate to add anti-foaming agents, such as silicone defoamers, or alkyl phosphates, preferably n-butyl phosphate.

Furthermore, other additives may be introduced into the composition, such as, UV-stabilizers, thickeners, and siccatives. Examples of siccatives (preferably utilized in combination with a binding agent based on a vegetable oil) are cobalt, zinc, ceric and/or manganous octoate and/or naphthanate.

As a rediluting agent for the preparation of ready to use agents from concentrates, use can be made of the above-named diluents or mixtures of diluents. Binding agents, additives, processing aids, dyes, pigments, UV-stabilizers, corrosion inhibitors and the like optionally may be used in combination with the diluents.

Additionally, the wood preservatives of the invention may contain a stabilizer or a mixture of stabilizers based on a phenol carrying aryl, alkyl or arylalkyl groups, a bisphenol or bisphenol derivative, a bis-hydroxyaryl alkane or bis-hydroxyaryl alkane derivative, a polyoxypolyphenyl alkane and/or at least one phosphatide.

With the aid of the stabilizer, the active agents are held chemically or physically stable in the wood preservative, even when the proportion of aliphatic hydrocarbons is very high.

The wood preservatives of the invention may be prepared in the form of a concentrate or a ready-to-use agent, such as a paint in the form of a scumble, particularly a paint scumble, or as an impregnating agent, the ready-to-use agent containing a corresponding amount of at least one diluent and optionally other processing agents and additives.

The invention relates further to the use of the active substances described above for the protection of constructional materials, particularly wood and wood substances, against damage or destruction by harmful organisms, particularly fungi and wood-eating insects. The material to be protected, particularly wood or wood substance, is treated according to known processes, such as painting, spraying, atomizing or impregnation, with an effective amount of the formulations of the invention.

The wood to be protected is treated with an amount of 50 to 1000 g, preferably 80 to 500 g of the agent of the invention per $m^2$ of wood surface.

The formulations of the invention are suitable both for combating an acute attack by and for preventive protection against insects or fungi. In an acute case, formulations are preferably used which contain both a juvenile hormone analogue and an ecdysone agonist. For prophylactic impregnation, however, it should generally be adequate to use only one of these two components preferably in association with a fungicide.

The invention will be explained in greater detail by means of the following examples.

General Recipes

| 1. Impregnation solvent | | |
|---|---|---|
| alkyd resin (such as linseed oil alkyd) | 7–12 | % b.w. |
| SHELLSOL AB ®, solvent naptha | 2–3 | % b.w. |
| Solvent naphtha K 60 | add 100 | % b.w. |
| 2. Priming solvent | | |
| alkyd resin (such as linseed oil alkyd) | 12–16 | % b.w. |
| SHELLSOL AB ®, solvent naptha | 2–3 | % b.w. |
| Solvent naphtha K 60 | add 100 | % b.w. |
| 3. Scumble solvent | | |
| alkyd resin (such as linseed oil alkyd) | 16–22 | % b.w. |
| SHELLSOL AB ®, solvent naptha | 3 | % b.w. |
| additive (siccative, antioxidant, | 1–2 | % b.w. |

-continued

| anti-precipitant) | | |
|---|---|---|
| inorg./org. pigments | 0.1–4 | % b.w. |
| solvent naphtha K 60 | add 100 | % b.w. |
| 4. Impregnation, aqueous | | |
| self-emulsifying alkyd resin | 7–12 | % b.w. |
| (soyya-linseed oil alkyd or the like | 2 | % b.w. |
| SHELLSOL AB ®, solvent naptha | add 100 | % b.w. |
| water | | |
| 5. Priming, aqueous | | |
| self-emulsifying alkyd resin | 8–12 | % b.w. |
| acrylate polymer | 2–4 | % b.w. |
| SHELLSOL AB ®, solvent naptha | 2 | % b.w. |
| butyl glycol | 3–4 | % b.w. |
| additives (siccative, antiprecipitant, antioxidant, pH stabilizer) | 2 | % b.w. |
| water | add 100 | % b.w. |
| 6. Scumbles, aqueous | | |
| alkyd resin/acrylate hybride | 16–22 | % b.w. |
| SHELLSOL AB ®, solvent naptha | 2 | % b.w. |
| additives (siccative, antiprecipitant, antioxidant, pH stabilizer) | 3–4 | % b.w. |
| inorg./org. pigments | 0.1–4 | % b.w. |
| butyl glycol | 4 | % b.w. |
| water | add 100 | % b.w. |
| 7. Impregnating agents | | |
| self-emulsifying alky resin | 30 | % b.w. |
| emulsifier | 10 | % b.w. |
| butyl diglycol | 30 | % b.w. |
| water | add 100 | % b.w. |
| Utilization concentration 1:9 | | |

The above general recipes were reacted with the following individually specified agents or combinations of agents, respectively dissolved in or in suspension in one of the components of the solvents.

EXAMPLE 1

The impregnation solvent from general recipe 1 was reacted with the following active substances:

| pyriproxyphene | 0.05% b.w. |
|---|---|
| fenoxycarb | 0.05% b.w. |
| propiconazole | 0.8% b.w. |

The impregnation formulation obtained was applied by painting, and was outstandingly effective against attacks by the house longhorn and fungi.

EXAMPLE 2

The impregnation solvent from general recipe 1 was reacted with the following active substances:

| pyriproxyphene | 0.01% b.w. |
|---|---|
| tebuphenozide | 0.1% b.w. |
| tebuconazole | 0.6% b.w. |

The impregnation formulation obtained was applied by painting or spraying, and was shown to be especially suitable for wood constructions endangered by insects and fingi.

EXAMPLE 3

The priming solvent of general recipe 2 was modified as follows: pyriproxyphene 0.01% b.w.

| pyriproxyphene | 0.01% b.w. |
|---|---|
| tebuphenozide | 0.5% b.w. |

Priming can be used advantageously for the treatment of wood surfaces to be subsequently coated.

EXAMPLE 4

The aqueous impregnation solvent from general recipe 4 was reacted with the following combination of active substances:

| fenoxycarb | 0.01% b.w. |
|---|---|
| pyriproxyphene | 0.01% b.w. |
| azadirachtin | 0.5% b.w. |
| myclobutanil | 1.5% b.w. |

A sprayable and paintable aqueous impregnation formulation was obtained which demonstrated outstanding protection against insect attack when applied by painting, dipping or spraying building timber.

EXAMPLE 5

Example 4 was repeated with the aqueous primer of general recipe 5, The aqueous primer was applied by painting, and provided a good coupling base for further painting.

EXAMPLE 6

The aqueous scumble of general formula 6 was reacted with the following combination of agents:

| pyriproxyphene | 0.01% b.w. |
|---|---|
| RH-0345 ® | 0.01% b.w. |
| Propiconazole | 0.6% b.w. |

This formulation was found to be outstandingly suitable as a wood preservation scumble for existing constructions requiring protection.

EXAMPLE 7

The same aqueous scumble used in example 6 was prepared using nuarimol as the fungicide instead of propiconazol.

EXAMPLE 8

A wood preservative for boiler pressure impregnation of constructional timber was prepared by reacting general recipe 7 with the following active substances:

| fenoxycarb | 0.05% b.w. |
|---|---|
| RH-0345 ® | 0.05% b.w. |
| quaternary ammonium compound | 10% b.w. |
| propiconazole | 0.4% b.w. |
| tebuconazole | 0.4% b.w. |

The impregnation agent can be used after dilution in a ratio of 1:9, and was found to be particularly suitable for the permanent impregnation of building timber.

EXAMPLE 9

The scumble solvent of general recipe 2 was reacted with the following combination of active substances:

| | |
|---|---|
| pyriproxyphene | 0.05% b.w. |
| azadirachtin | 0.05% b.w. |
| phenarimol | 1.2% b.w. |

The scumble was found to be particularly suitable in combating attacks by harmful insects in existing timber constructions in inhabited buildings.

EXAMPLE 10

The impregnation solvent of general recipe 4 was reacted with the following combination of active substances:

| | |
|---|---|
| pyriproxyphene | 0.05% b.w. |
| fenoxycarb | 0.05% b.w. |
| propiconazole | 0.08% b.w. |
| quaternary ammonium compound | 10% b.w. |

The impregnation formulation was demonstrated to be particularly suitable for the treatment of existing timber constructions, such as roof timbering, to prevent an attack and also to combat such attack.

EXAMPLE 11

Example 10 was repeated with the following combination of active agents:

| | |
|---|---|
| pyriproxyphene | 0.05% b.w. |
| azadirachtin | 0.05% b.w. |
| phenarimol | 1.0% b.w. |
| quaternary ammonium compound | 12.5% b.w. |

What is claimed is:

1. A wood preservative for the protection of wood against dry-wood- destroying insects, which comprises a wood preservative carrier and the combination of at least one insect juvenile hormone or its analogue or mimetic with at least one an ecdysone agonist or its analogue or mimetic in a concentration of 0.5 to 0.00005 % by weight, related to the entire formulation, and optionally, one or more triazole compounds to achieve a synergistic increase in effectiveness of said formulation.

2. A wood preservative according to claim 1, wherein the insect juvenile hormone is selected from the group consisting of fenoxycarb, pyriproxyphene, kinoprene, methoprene and hydroprene, and said ecdysone agonist is selected from the group consisting of tebufenozide, halofenozide, tebufenozide analogues, azadirachtin and azadiractanin.

3. A wood preservative according to claim 2, wherein the insect juvenile hormone is selected from the group consisting of fenoxycarb and pyriproxyphene.

4. A wood preservative according to claim 2, wherein the ecdysone agonist is selected from the group consisting of tebufenozide, halofenozide and azadiractin.

5. A wood preservative according to claim 1, comprising one or more of said insect juvenile hormones in a concentration of from 0.005 to 0.001 % by weight.

6. A wood preservative according to claim 1, comprising one or more fungicides.

7. A wood preservative according to claim 6, wherein the fungicide is said triazole fungicide.

8. A wood preservative according to claim 7, wherein said triazole fungicide is selected from the group consisting of propiconazole, tebuconazole, azaconazole, phenbuconazole, myclobutanil and triadimenol.

9. A wood preservative according to claim 6, comprising a non-triazole fungicide.

10. A wood preservative according to claim 9, wherein said non-triazole fungicide is selected from the group consisting of nuarimol, phenarimol, IPBC, tolylfluanide, dichlofluanide and TIAA.

* * * * *

UNITED STATES PATENT AND TRADEMARK OFFICE
CERTIFICATE OF CORRECTION

PATENT NO. : 6,248,159 B1  Page 1 of 1
DATED : June 19, 2001
INVENTOR(S) : Heinrich Poppen et al.

It is certified that error appears in the above-identified patent and that said Letters Patent is hereby corrected as shown below:

Title page,
Item [62], "on Jun. 9, 1998" should read -- as PCT/EP96/04270 on Sept. 30, 1996 --.

Signed and Sealed this

Twenty-ninth Day of January, 2002

Attest:

JAMES E. ROGAN
*Attesting Officer*  *Director of the United States Patent and Trademark Office*